(12) United States Patent
Benson et al.

(10) Patent No.: US 8,143,422 B2
(45) Date of Patent: Mar. 27, 2012

(54) BENZIMIDAZOLE DERIVATIVES

(75) Inventors: Gregory Martin Benson, Therwil (CH); Konrad Bleicher, Freiburg (DE); Song Feng, Shanghai (CN); Uwe Grether, Efringen-Kirchen (DE); Bernd Kuhn, Reinach BL (CH); Rainer E. Martin, Basel (CH); Jean-Marc Plancher, Hagenthal-le-Bas (FR); Hans Richter, Grenzach-Wyhlen (DE); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 148 days.

(21) Appl. No.: 12/577,765

(22) Filed: Oct. 13, 2009

(65) Prior Publication Data

US 2010/0093818 A1    Apr. 15, 2010

(30) Foreign Application Priority Data

Oct. 15, 2008    (EP) .................... 08166706

(51) Int. Cl.
| | |
|---|---|
| *A61K 31/4184* | (2006.01) |
| *A61K 31/4439* | (2006.01) |
| *C07D 235/06* | (2006.01) |
| *C07D 403/12* | (2006.01) |

(52) U.S. Cl. ............. 548/309.7; 514/338; 514/394; 546/273.4

(58) Field of Classification Search ............ 548/309.7
See application file for complete search history.

(56) References Cited

U.S. PATENT DOCUMENTS 7,825,258 B2 * 11/2010 Benson et al. ............ 548/309.7

FOREIGN PATENT DOCUMENTS

| WO | WO 2008/000643 | 1/2008 |
| WO | WO 2009/062874 | 5/2009 |

OTHER PUBLICATIONS

Golub et al., Science, vol. 286, Oct. 15, 1999, pp. 531-537.*

* cited by examiner

*Primary Examiner* — Laura L. Stockton
(74) *Attorney, Agent, or Firm* — George W. Johnston; Dennis P. Tramaloni

(57) ABSTRACT

The invention is concerned with novel benzimidazole derivatives of formula (I)

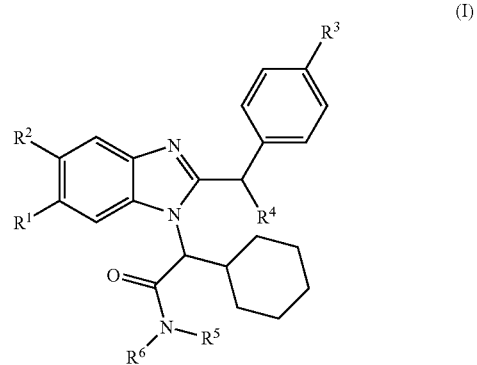

(I)

wherein $R^1$ to $R^6$ are as defined in the description and in the claims, as well as physiologically acceptable salts and esters thereof. These compounds can be used as medicaments.

16 Claims, No Drawings

BENZIMIDAZOLE DERIVATIVES

PRIORITY TO RELATED APPLICATION(s)

This application claims the benefit of European Patent Application No. 08166706.5, filed Oct. 15, 2008, which is hereby incorporated by reference in its entirety.

FIELD OF THE INVENTION

The present invention is generally concerned with novel benzimidazole derivatives, their manufacture and their use as medicaments. More specifically, the invention relates to novel benzimidazole derivatives of compounds of formula (I).

BACKGROUND OF THE INVENTION

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. Identification of a nuclear receptor for bile acids. *Science* 1999, 284, 1362-1365]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXRalpha and blocks their transcriptional functions [Lu, T. T., Makishima, M., Repa, J. J., Schoonjans, K., Kerr, T. A., Auwerx, J. and Mangelsdorf, D. J. Molecular basis for feedback regulation of bile acid synthesis by nuclear receptors. *Mol. Cell.* 2000, 6, 507-515]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tarr, P. T., Jones, S. A., Anisfeld, A. M., Stoltz, C. M., Tontonoz, P., Kliewer, S., Willson, T. M. and Edwards, P. A. Regulation of multidrug resistance-associated protein 2 (ABCC2) by the nuclear receptors pregnane X receptor, farnesoid X-activated receptor, and constitutive androstane receptor. *J. Biol. Chem.* 2002, 277, 2908-2915; Ananthanarayanan, M., Balasubramanian, N., Makishima, M., Mangelsdorf, D. J. and Suchy, F. J. Human bile salt export pump promoter is transactivated by the farnesoid X receptor/bile acid receptor. *J. Biol. Chem.* 2001, 276, 28857-28865]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. Hepatoprotection by the farnesoid X receptor agonist GW4064 in rat models of intra- and extra-hepatic cholestasis. *J. Clin. Invest.* 2003, 112, 1678-1687; Sinal, C. J., Tohkin, M., Miyata, M., Ward, J. M., Lambert, G. and Gonzalez, F. J. Targeted disruption of the nuclear receptor FXR/BAR impairs bile acid and lipid homeostasis. *Cell* 2000, 102, 731-744]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines their ability to solubilize cholesterol. FXR activation decreases the size and changes the composition of the bile acid pool, decreasing the intestinal solubilization of cholesterol, effectively blocking its absorption. Decreased absorption would be expected to result in lower plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. *J. Biol. Chem.* 2006, 281, 807-812]. FXR also decreases hepatic synthesis of triglycerides by repressing SREBP1-c expression by an alternate pathway involving SHP and LXRalpha. Thus compounds that activate FXR may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol>240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple comorbidities including dyslipidemia and insulin resistance, as well as hypertension, endothelial dysfunction and inflammatory atherosclerosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

SUMMARY OF THE INVENTION

The present invention is concerned with novel benzimidazole derivatives, their manufacture and their use as medicaments. In particular, the invention relates to compounds of formula (I)

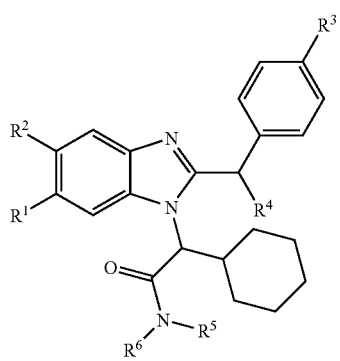

wherein
$R^1$ is hydrogen or halogen;
$R^2$ is hydrogen or halogen;
$R^3$ is hydrogen or halogen;
$R^4$ is hydroxy or alkoxy;
$R^5$ is hydrogen or alkyl;
$R^6$ is cyclohexyl, phenyl or pyridyl, wherein cyclohexyl, phenyl and pyridyl are substituted with hydroxy, carboxy, carboxyalkyl, carboxyalkoxy, carboxycycloalkoxy or tetrazolyl, and wherein cyclohexyl, phenyl and pyridyl are optionally further substituted with one or two substituents independently selected from halogen, alkyl, haloalkyl, alkoxy, haloalkoxy and cyano;
and pharmaceutically acceptable salts and esters thereof.

The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

DETAILED DESCRIPTION OF THE INVENTION

A. Definitions

Unless otherwise indicated, the following definitions are set forth to illustrate and define the meaning and scope of the various terms used to describe the invention herein. All references cited herein are hereby incorporated by reference in their entirety.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl. The term "lower alkyl" refers to a C1-C4 alkyl group.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy and most preferred methoxy.

The term "halogen", alone or in combination, signifies fluorine, chlorine, bromine or iodine and preferably fluorine or chlorine.

The term "cycloalkoxy", alone or in combination, signifies a group of the formula cycloalkyl-O— in which the term "cycloalkyl" signifies a cycloalkyl ring with 3 to 8 carbon atoms and preferably a cycloalkyl ring with 3 to 6 carbon atoms. Examples of C3-C8 cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. A preferred example of cycloalkoxy is cyclopropyloxy.

The term "haloalkyl", alone or in combination, signifies an alkyl group as defined above wherein one or more hydrogen atoms, preferably one, two or three hydrogen atoms, are replaced with a halogen atom. A preferred example of haloalkyl is trifluoromethyl.

The term "haloalkoxy", alone or in combination, signifies a alkoxy group as defined above wherein one or more hydrogen atoms, preferably one, two or three hydrogen atoms, are replaced with a halogen atom. A preferred example of haloalkoxy is trifluoromethoxy.

The term "carboxy", alone or in combination, signifies the group —COOH.

The term "cyano", alone or in combination, signifies the group —CN.

The term "oxy", alone or in combination, signifies the —O— group.

Compounds of formula (I) can form pharmaceutically acceptable addition salts. Examples of such pharmaceutically acceptable salts are salts of compounds of formula (I) with physiologically compatible mineral bases, such as alkaline, earth-alkaline and ammonium or substituted ammonium salts such as e.g., Na-, K-, Ca- and trimethylammonium salt. The term "pharmaceutically acceptable salts" refers to such salts.

The term "pharmaceutically acceptable esters" embraces derivatives of the compounds of formula (I), in which a carboxy group has been converted to an ester. Alkyl, hydroxyalkyl, alkoxy-alkyl, amino-alkyl, mono- or di-alkyl-amino-alkyl, morpholino-alkyl, pyrrolidino-alkyl, piperidino-alkyl, piperazino-alkyl, alkyl-piperazino-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

DETAILED DESCRIPTION

The present invention is concerned with novel benzimidazole derivatives, their manufacture and their use as medicaments. In particular, the invention relates to compounds of formula (I)

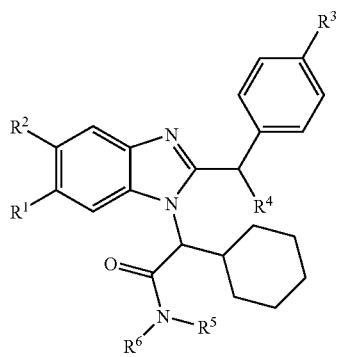

wherein
$R^1$ is hydrogen or halogen;
$R^2$ is hydrogen or halogen;
$R^3$ is hydrogen or halogen;
$R^4$ is hydroxy or alkoxy;
$R^5$ is hydrogen or alkyl;
$R^6$ is cyclohexyl, phenyl or pyridyl, wherein cyclohexyl, phenyl and pyridyl are substituted with hydroxy, carboxy, carboxyalkyl, carboxyalkoxy, carboxycycloalkoxy or tetrazolyl, and wherein cyclohexyl, phenyl and pyridyl are optionally further substituted with one or two substituents independently selected from halogen, alkyl, haloalkyl, alkoxy, haloalkoxy and cyano;
and pharmaceutically acceptable salts and esters thereof.

Preferred compounds of formula (I) as described above are those, wherein
$R^6$ is of formula (II)

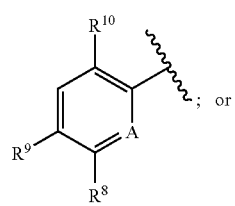

of formula (III)

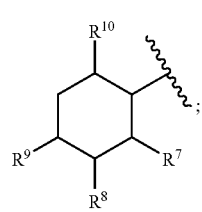

wherein
A is nitrogen or $CR^7$;
$R^7$ is hydrogen, halogen, alkyl, haloalkyl, alkoxy, haloalkoxy or cyano;
$R^{10}$ is hydrogen, halogen, alkyl, haloalkyl, alkoxy, haloalkoxy or cyano; and wherein
one of $R^8$ and $R^9$ is selected from hydroxy, carboxy, carboxyalkyl, carboxyalkoxy carboxycycloalkoxy and tetrazolyl and the other one is hydrogen.

Further preferred are the compounds of formula (I), wherein
$R^6$ is of formula (II) of formula (III)

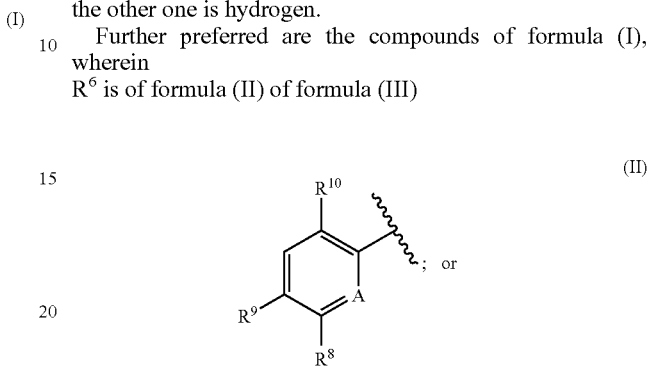

A is $CR^7$;
$R^7$ is hydrogen, halogen, alkyl, haloalkyl, haloalkoxy or cyano;
$R^{10}$ is hydrogen or halogen;
one of $R^8$ and $R^9$ is selected from hydroxy, carboxy, carboxyalkyl, carboxyalkoxy and carboxycycloalkoxy and the other one is hydrogen.

Particularly preferred are the compounds of formula (I), wherein
$R^6$ is of formula (II)

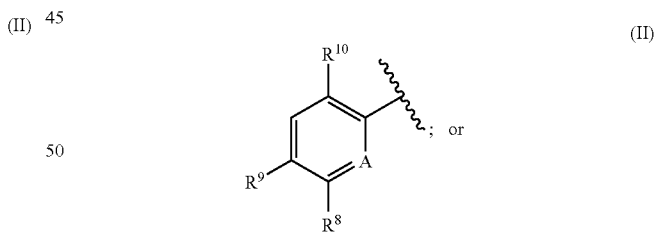

of formula (III)

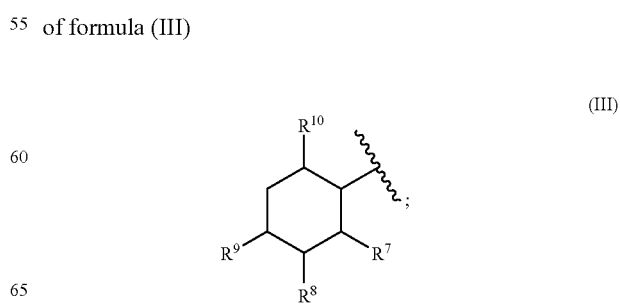

A is $CR^7$;
$R^7$ is hydrogen, fluorine, chlorine, methyl, trifluoromethyl, trifluoromethoxy or cyano;
$R^{10}$ is hydrogen or fluorine;
one of $R^8$ and $R^9$ is selected from hydroxy, carboxy, carboxymethyl, carboxyethyl, carboxyethoxy and carboxycyclopropoxy and the other one is hydrogen.

Other preferred compounds of formula (I) include wherein $R^6$ is of formula (II)

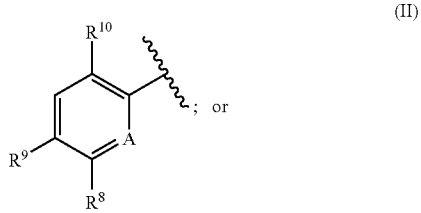

of formula (III)

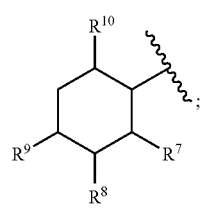

wherein A, $R^7$ and $R^{10}$ are as defined above and wherein one of $R^8$ and $R^9$ is selected from carboxy, carboxymethyl, carboxyethyl, carboxyethoxy and carboxycyclopropoxy and the other one is hydrogen.

Further preferred are the compounds of formula (I) wherein
$R^6$ is of formula (II)

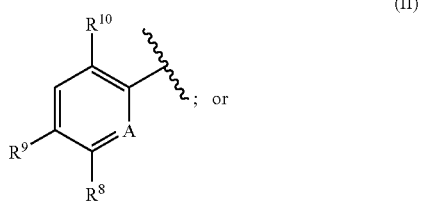

of formula (III)

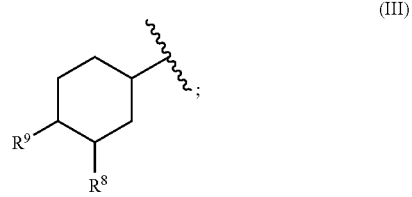

wherein A, and $R^7$-$R^{10}$ are as defined above.
Also particularly preferred are the compounds of formula (I), wherein $R^7$ is hydrogen, fluorine, chlorine or methyl.

Further preferred are the compounds of formula (I), wherein $R^{10}$ is hydrogen or fluorine, with hydrogen particularly preferred.

The compounds of formula (I), wherein A is nitrogen are also preferred.

Particularly preferred are the compounds of formula (I), wherein one of $R^8$ and $R^9$ is selected from carboxy, carboxymethyl, carboxyethyl, carboxyethoxy and carboxycyclopropoxy and the other one is hydrogen.

Further preferred are the compounds of formula (I), wherein $R^9$ is carboxy. Also preferred are the compounds of formula (I), wherein $R^4$ is hydroxy or methoxy and particularly preferred are the compounds of formula (I), wherein $R^4$ is methoxy.

The compounds of formula (I), wherein $R^3$ is hydrogen or fluorine are preferred and particularly the compounds of formula (I), wherein $R^3$ is hydrogen.

The compounds of formula (I), wherein $R^1$ is fluorine are preferred. The compounds of formula (I), wherein $R^2$ is fluorine are also preferred. The compounds of formula (I), wherein $R^1$ and $R^2$ are both fluorine at the same time are particularly preferred.

Also preferred are the compounds of formula (I), wherein $R^5$ is hydrogen.

Further preferred are the compounds of formula (I), wherein $R^6$ is cyclohexyl, phenyl or pyridyl, wherein cyclohexyl, phenyl and pyridyl are substituted with hydroxy, carboxy, carboxymethyl, carboxyethyl, carboxyethoxy, carboxycyclopropoxy or tetrazolyl, and wherein phenyl and pyridyl are optionally further substituted with one or two substituents independently selected from fluoro, chloro, methyl, trifluoromethoxy, cyano and trifluoromethyl. Particularly preferred are the compounds of formula (I), wherein $R^6$ is carboxycyclohexyl, carboxymethylcyclohexyl, carboxyphenyl, phenyl substituted with carboxy and fluoro, phenyl substituted with carboxy and methyl, phenyl substituted with carboxy and chloro, carboxypyridyl, phenyl substituted with carboxy and trifluoromethoxy, phenyl substituted with carboxy and cyano and fluoro, carboxyethoxyphenyl, phenyl substituted with carboxy and cyano, phenyl substituted with carboxy and trifluoromethyl, carboxycyclopropoxyphenyl or phenyl substituted with carboxyethyl and fluoro.

In particular, preferred are the compounds of formula (Ia)

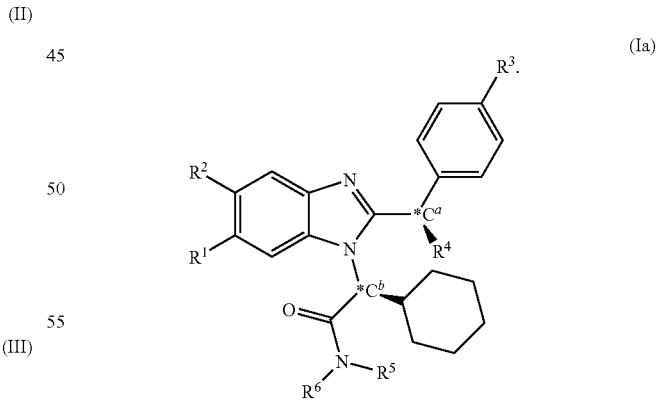

Preferred are the compounds of formula (I) wherein the asymmetric carbon $*C^a$ is of (S) configuration and particularly preferred of the (R) configuration according to the Cahn-Ingold-Prelog Convention.

Preferred are the compounds of formula (I) wherein the asymmetric carbon $*C^b$ is of (R) configuration and particularly preferred of the (S) configuration according to the Cahn-Ingold-Prelog Convention.

In a particular embodiment of the invention, the compounds of formula (I) are selected from 4-{(R)-2-Cyclohexyl-2-[5,6-difluoro-2-((S)-methoxy-phenyl-methyl)-benzoimidazol-1-yl]-acetylamino}-benzoic acid;

4-{(S)-2-Cyclohexyl-2-[5,6-difluoro-2-((S)-methoxy-phenyl-methyl)-benzoimidazol-1-yl]-acetylamino}-benzoic acid;

4-{(R)-2-Cyclohexyl-2-[5,6-difluoro-2-((R)-methoxy-phenyl-methyl)-benzoimidazol-1-yl]-acetylamino}-benzoic acid;

4-{(S)-2-Cyclohexyl-2-[5,6-difluoro-2-((R)-methoxy-phenyl-methyl)-benzoimidazol-1-yl]-acetylamino}-benzoic acid;

4-{(R)-2-Cyclohexyl-2-[5,6-difluoro-2-((S)-methoxy-phenyl-methyl)-benzoimidazol-1-yl]-acetylamino}-3-fluoro-benzoic acid;

4-{(S)-2-Cyclohexyl-2-[5,6-difluoro-2-((S)-methoxy-phenyl-methyl)-benzoimidazol-1-yl]-acetylamino}-3-fluoro-benzoic acid;

4-{(R)-2-Cyclohexyl-2-[5,6-difluoro-2-((R)-methoxy-phenyl-methyl)-benzoimidazol-1-yl]-acetylamino}-3-fluoro-benzoic acid;

4-{(S)-2-Cyclohexyl-2-[5,6-difluoro-2-((R)-methoxy-phenyl-methyl)-benzoimidazol-1-yl]-acetylamino}-3-fluoro-benzoic acid;

4-{(R)-2-Cyclohexyl-2-[5,6-difluoro-2-((S)-methoxy-phenyl-methyl)-benzoimidazol-1-yl]-acetylamino}-3-methyl-benzoic acid;

4-{(S)-2-Cyclohexyl-2-[5,6-difluoro-2-((S)-methoxy-phenyl-methyl)-benzoimidazol-1-yl]-acetylamino}-3-methyl-benzoic acid;

4-{(R)-2-Cyclohexyl-2-[5,6-difluoro-2-((R)-methoxy-phenyl-methyl)-benzoimidazol-1-yl]-acetylamino}-3-methyl-benzoic acid;

4-{(S)-2-Cyclohexyl-2-[5,6-difluoro-2-((R)-methoxy-phenyl-methyl)-benzoimidazol-1-yl]-acetylamino}-3-methyl-benzoic acid;

3-Chloro-4-{(R)-2-cyclohexyl-2-[5,6-difluoro-2-((S)-methoxy-phenyl-methyl)-benzoimidazol-1-yl]-acetylamino}-benzoic acid;

3-Chloro-4-{(S)-2-cyclohexyl-2-[5,6-difluoro-2-((S)-methoxy-phenyl-methyl)-benzoimidazol-1-yl]-acetylamino}-benzoic acid;

3-Chloro-4-{(R)-2-cyclohexyl-2-[5,6-difluoro-2-((R)-methoxy-phenyl-methyl)-benzoimidazol-1-yl]-acetylamino}-benzoic acid;

3-Chloro-4-{(S)-2-cyclohexyl-2-[5,6-difluoro-2-((R)-methoxy-phenyl-methyl)-benzoimidazol-1-yl]-acetylamino}-benzoic acid;

6-{(R)-2-Cyclohexyl-2-[5,6-difluoro-2-((S)-methoxy-phenyl-methyl)-benzoimidazol-1-yl]-acetylamino}-nicotinic acid;

6-{(S)-2-Cyclohexyl-2-[5,6-difluoro-2-((S)-methoxy-phenyl-methyl)-benzoimidazol-1-yl]-acetylamino}-nicotinic acid;

6-{(R)-2-Cyclohexyl-2-[5,6-difluoro-2-((S)-methoxy-phenyl-methyl)-benzoimidazol-1-yl]-acetylamino}-nicotinic acid;

6-{(S)-2-Cyclohexyl-2-[5,6-difluoro-2-((S)-methoxy-phenyl-methyl)-benzoimidazol-1-yl]-acetylamino}-nicotinic acid;

(trans-4-{2-Cyclohexyl-2-[5-fluoro-2-((R)-methoxy-phenyl-methyl)-benzoimidazol-1-yl]-acetylamino}-cyclohexyl)-acetic acid;

trans-4-{2-Cyclohexyl-2-[5-fluoro-2-((R)-methoxy-phenyl-methyl)-benzoimidazol-1-yl]-acetylamino}-cyclohexanecarboxylic acid;

4-(2-Cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-hydroxy-methyl]-benzoimidazol-1-yl}-acetylamino)-3-fluoro-benzoic acid;

3-Chloro-4-(2-cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-hydroxy-methyl]-benzoimidazol-1-yl}-acetylamino)-3-methyl-benzoic acid;

3-(2-Cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-fluoro-benzoic acid;

3-Chloro-4-(2-cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-methyl-benzoic acid;

3-(2-Cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-trifluoromethoxy-benzoic acid;

3-Cyano-4-(2-cyclohexyl-2-{5,6-difluoro-2-[(4-fluoro-phenyl)-methoxy-methyl]-benzoimidazol-1-yl}-acetylamino)-5-fluoro-benzoic acid;

2-[4-(2-Cyclohexyl-2-{5,6-difluoro-2-[(4-fluoro-phenyl)-methoxy-methyl]-benzoimidazol-1-yl}-acetylamino)-phenoxy]-propionic acid;

6-(2-Cyclohexyl-2-{5,6-difluoro-2-[(4-fluoro-phenyl)-methoxy-methyl]-benzoimidazol-1-yl}-acetylamino)-nicotinic acid;

3-Cyano-4-(2-cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-trifluoromethyl-benzoic acid;

1-[4-(2-Cyclohexyl-2-{5,6-difluoro-2-[(4-fluoro-phenyl)-methoxy-methyl]-benzoimidazol-1-yl}-acetylamino)-phenoxy]-cyclopropanecarboxylic acid;

3-[4-(2-Cyclohexyl-2-{5,6-difluoro-2-[(4-fluoro-phenyl)-methoxy-methyl]-benzoimidazol-1-yl}-acetylamino)-3-fluoro-phenyl]-propionic acid;

Trans-[4-(2-cyclohexyl-2-{5,6-difluoro-2-[(4-fluoro-phenyl)-hydroxy-methyl]-benzoimidazol-1-yl}-acetylamino)-cyclohexyl]-acetic acid; and

[4-(2-Cyclohexyl-2-{5,6-difluoro-2-[(4-fluoro-phenyl)-methoxy-methyl]-benzoimidazol-1-yl}-acetylamino)-cyclohexyl]-acetic acid.

In a particularly preferred embodiment of the invention, the compounds of formula (I) are selected from 4-{(S)-2-Cyclohexyl-2-[5,6-difluoro-2-((R)-methoxy-phenyl-methyl)-benzoimidazol-1-yl]-acetylamino}-benzoic acid;

4-{(S)-2-Cyclohexyl-2-[5,6-difluoro-2-((R)-methoxy-phenyl-methyl)-benzoimidazol-1-yl]-acetylamino}-3-fluorobenzoic acid;

4-{(S)-2-Cyclohexyl-2-[5,6-difluoro-2-((R)-methoxy-phenyl-methyl)-benzoimidazol-1-yl]-acetylamino}-3-methyl-benzoic acid;

3-Chloro-4-{(S)-2-cyclohexyl-2-[5,6-difluoro-2-((R)-methoxy-phenyl-methyl)-benzoimidazol-1-yl]-acetylamino}-benzoic acid; and 6-{(S)-2-Cyclohexyl-2-[5,6-difluoro-2-((R)-methoxy-phenyl-methyl)-benzoimidazol-1-yl]-acetylamino}-nicotinic acid.

The compounds of formula (I) have one or more asymmetric C atoms and can therefore exist as an enantiomeric mixture, diastereomeric mixture or as optically pure compounds.

Insofar as their preparation is not described in the examples, the compounds of formula (I) as well as all intermediate products can be prepared according to analogous methods or according to the methods set forth hereunder. Starting materials are commercially available, are known in the art, or can be prepared by methods analogous to those described herein.

Compounds of formula (I) according to the present invention may be prepared for example by the methods and procedures given below. A typical procedure for the preparation of compounds of formula I is illustrated in Scheme 1.

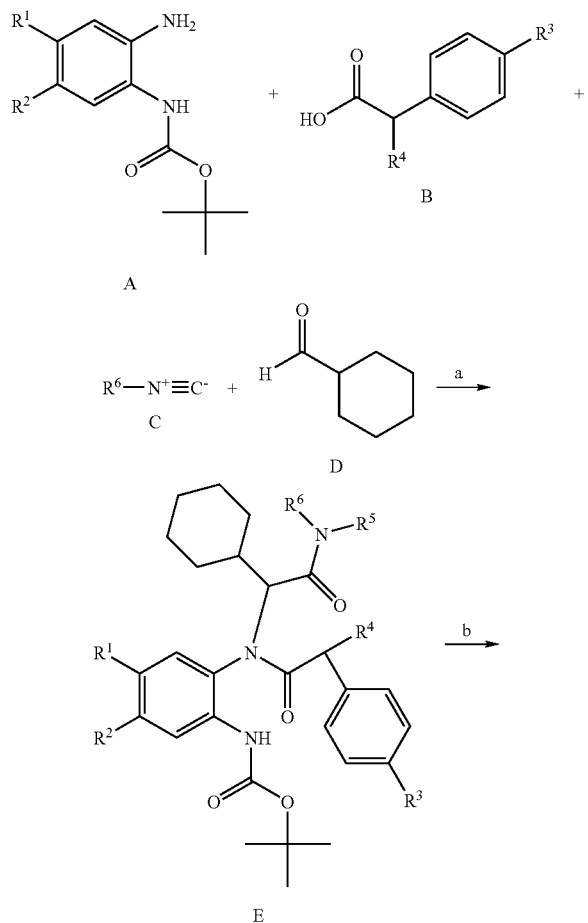

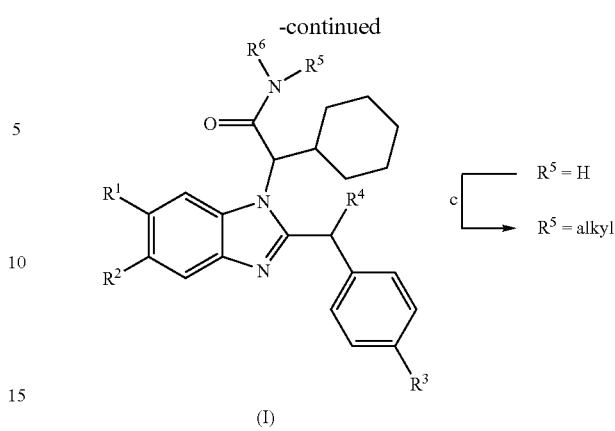

In this approach a mono tert-butyloxycarbonyl-protected aryl ortho diamine A, a carboxylic acid B, an isonitrile C, and an aldehyde D are condensed in an organic solvent, such as for example methanol, to provide the bis-amide E in an Ugi-type multi-component condensation (Scheme 1, step a; typical procedures may for example be found in "The Peptides" by Gross & Meienhofer Vol. 2, Academic Press, N.Y., 1980, pp 365-381). Bis-amide E is deprotected with a suitable acid (e.g. trifluoroacetic acid or hydrochloric acid) and spontaneously undergoes cyclisation to the desired benzimidazole I (Scheme 1, step b). Typical procedures applicable to this approach were described e.g. by P. Tempest, V. Ma, S. Thomas, Z. Hua, M. G. Kelly and C. Hulme *Tetrahedron Lett.* 2001, 42, 4959-4962 and P. Tempest, V. Ma, M. G. Kelly, W. Jones and C. Hulme *Tetrahedron Lett.* 2001, 42, 4963-4968, or by W. Zhang and P. Tempest, *Tetrahedron Lett.* 2004, 45, 6757-6760. Benzimidazoles I may optionally be N-alkylated by deprotonation with a strong base (e.g. NaH or LiHMDA) in a suitable solvent (e.g. tetrahydrofuran) and subsequent treatment with an alkylating agent $R^5$—X, with X being a typical leaving group such as e.g. Cl, Br, I, —$SO_2$alkyl, —$SO_2$fluoroalkyl, —$SO_2$aryl (Scheme 1, step c).

Many of the building blocks A-D are commercially available. If not, they may be prepared from commercially available starting materials using procedures described in literature and typically known to those skilled in the art.

Tert-butyloxycarbonyl-protected aryl ortho diamines A are commercially available, or may be prepared from the corresponding unprotected diamine by treatment with di-tert-butyl dicarbonate in an organic solvent, such as methanol, in the presence of iodine as catalyst, as described e.g. by R. Varala, S, Nuvula and S. R. Adapa, *J. Org. Chem.*, 2006, 71, 8283, or by treatment with di-tert-butyl dicarbonate in a suitable organic solvent, such as tetrahydrofuran, in the presence of a base such as e.g. diisopropylethylamine.

α-Alkoxyaryl acetic acids B may be synthesized by base-catalyzed condensation of aldehydes F with haloforms (e.g. chloroform) and alcohols (e.g. methanol) as described by W. Reeve, C. W. Woods, *J. Am. Chem. Soc.* 1960, 82, 4062-4066 and A. Carlsson, H. Corrodi, B. Waldeck *Helv. Chico. Acta* 1963, 46, 2271-2285 (Scheme 2, step a).

Scheme 2

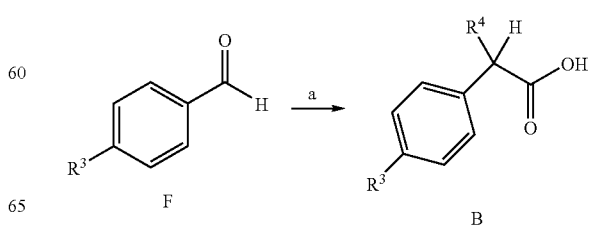

An alternative way to the synthesis of α-alkoxyaryl acetic acids B consists in lithiation of suitable compounds G with a strong base such as n-BuLi in an inert solvent such as anhydrous tetrahydrofuran or ether at low temperatures (e.g. −100° C.) under an atmosphere of nitrogen or argon. Slow addition of glyoxylic acid ethyl ester to a lithium nucleophile generated such affords α-hydroxyaryl acetic acids of general structure H (Scheme 3, step a). Alkylation of hydroxy acids H may be conducted with suitable halides, mesylates, tosylates (or alcohols transformed into any other suitable leaving group X) in a solvent such as DMF, dichloromethane, dichloroethane or acetone at ambient or elevated temperatures using conventional heating or heating by microwave irradiation with the addition of a suitable tertiary amine base (e.g. triethylamine, N-ethyldiisopropylamine) or an inorganic base (e.g. $Cs_2CO_3$, $K_2CO_3$) or silver(I) oxide ($Ag_2O$) or by analogous alkylation reactions (Scheme 3, step b). Alternatively, target structures of formula I might be accessible by Mitsunobu reaction (D. L. Hughes, The Mitsunobu Reaction, in *Organic Reactions*, Volume 42, 1992, John Wiley & Sons, New York; pp. 335-656) applying alcohols activated by a mixture of a phosphine, such as a trialkylphosphine, e.g. tributylphosphine (($n$-$Bu$)$_3$P), or triarylphosphine, e.g. triphenylphosphine ($Ph_3P$) and the like, and an azo-compound such as diethyl azodicarboxylate (DEAD), diisopropyl azodicarboxylate (DIAD) or di-tent-butyl azodicarboxylate and the like, in a solvent commonly used for such transformations, such as tetrahydrofuran, toluene, dichloromethane and the like. There is no particular restriction to the nature of the solvent to be employed, provided that it has no adverse effect on the reaction or the reagents involved and that it can dissolve the reagents, at least to some extent. The reaction can take place over a wide range of temperatures ranging from ambient temperature to the reflux temperature of the solvent employed. Ester hydrolysis of compounds J to afford target structures B may be achieved by applying standard reaction conditions used for such types of conversions known to a person skilled in the art, such as stirring with alkaline hydroxides (e.g. LiOH, NaOH, KOH) in a solvent mixture consisting typically of tetrahydrofuran and water at room or elevated temperatures, whereby conventional heating or heating by microwave irradiation might be applied.

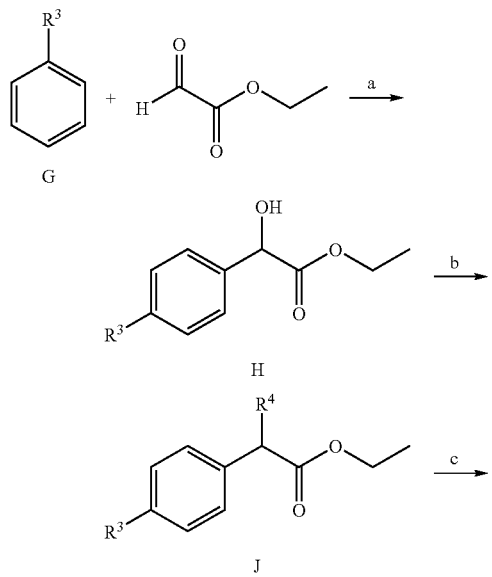

Scheme 3

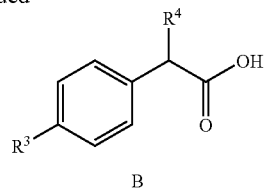

B

The isonitriles C are either commercially available, or may be obtained for example by dehydration of the corresponding formamide $R^6$—NH—CHO with a suitable reagent such as e.g. triphosgene, phosgene, $POCl_3$ or $Me_2N\!\!=\!\!CH^+Cl\ Cl^-$ or by reaction of the corresponding amine $R^6$—$NH_2$ with $CHCl_3$ and NaOH in a suitable solvent, such as methanol.

Aldehydes D are either commercially available or may be prepared by numerous methods known to the person skilled in the art. Appropriate synthesis methods include for example the reduction of the corresponding carboxylic acid esters with a suitable reducing agent (e.g. diisobutylaluminium hydride at low temperature, or $LiAlH_4$ at elevated or ambient temperature) in a suitable solvent, followed by oxidation of the primary alcohol (e.g. with tetrapropylammonium perruthenate(VII), activated $MnO_2$ or Dess-Martin periodinane) to yield aldehydes D.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, $3^{rd}$ Ed., 1999, Wiley, New York) can be introduced before the critical step applying methods well known in the art. Such protecting groups can be removed at a later stage of the synthesis using standard methods described in the literature.

If compounds A, B, C or D contain stereogenic centers, compounds (I) may be obtained as mixtures of diastereomers or enantiomers, which can be separated by methods well known in the art, for example (chiral) HPLC or crystallisation. Racemic compounds can for example be separated into their antipodes via diastereomeric salts by crystallisation with optically pure acids or bases or by separation of the antipodes by specific chromatographic methods using either a chiral adsorbent or a chiral eluant.

If desired or required, functional groups present in (I) (such as —$CO_2$alkyl, amino groups, cyano groups and others) may be derivatized to other functional groups using typical standard procedures known to those skilled in the art (e.g. reduction of —$CO_2$alkyl to —$CH_2OH$ with $LiAlH_4$, hydrolysis of —$CO_2$alkyl to —$CO_2H$ and subsequent optional conversion to an amide, acylation of amino groups).

$R^6$ as present in (I) after steps a and b, or steps a, b and c in the above scheme may be transformed into, or replaced by other $R^6$ using one or a sequence of reaction steps. Two possible examples are given below:

a) $R^6\!\!=\!\!CH_2Ph$ may for instance be removed using debenzylation conditions (e.g. hydrogenolysis in a solvent such as methanol in presence of a catalyst such as Pd(0) on charcoal powder) and a new $R^6$ can be introduced e.g. by deprotonation of the resulting $CONHR^5$ with a strong base (e.g. lithium hexamethyldisilylamide) and treatment with an alkylating agent $R^6$—X (X being a typical leaving group such as e.g. Cl, Br, I, —$SO_2$alkyl, —$SO_2$fluoroalkyl, —$SO_2$aryl, and $R^6$ being $C_{1-10}$-alkyl, lower-alkoxy-lower-alkyl, lower-alkoxy-carbonyl-lower-alkyl, cycloalkyl, cycloalkyl-lower-alkyl, aryl-lower-alkyl, di-aryl-lower-alkyl, heteroaryl-lower-alkyl or heterocyclyl-lower-alkyl) or alternatively by a Pd(II)-promoted coupling with R⁶—X (R⁶ being aryl or heteroaryl and X being Cl, Br, I or —OSO₂CF₃).

b) Hydrolysis of the —CCyCONR⁵R⁶-moiety of (I) to —CCyCOOH L (Cy=cyclohexyl) may be carried out using suitable conditions such as heating in isopropanol in presence of NaOH or LiOH. A new amide bond may be formed using an amine HNR⁵R⁶ and a typical peptide coupling reagent such as e.g. N,N'-carbonyldiimidazole (CDI), N,N'-dicyclohexylcarbodiimide (DCC), 1-(3-dimethyl-aminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluoroborate (TBTU) and the like, in a presence of a suitable basic amine (e.g. triethylamine, N-ethyldiisopropylamine, pyridine) in a suitable solvent (e.g. dichloromethane, acetonitrile or N,N-dimethylformamide). Preferred coupling agents are 1-(3-dimethylaminopropyl)-3-ethylcarbodiimide hydrochloride (EDCI) or N,N'-carbonyldiimidazole (CDI). Alternatively a new amide bond may be formed by converting the acid —CCyCOOH into the corresponding acid chloride —CCyCOCl by reaction with a suitable chlorinating reagent, e.g. thionyl chloride at reflux, or thionyl chloride in the presence of a suitable base, e.g. pyridine, in a suitable solvent, e.g. dichloromethane at 0° C. to room temperature (see for example F. Matsuda, S. Itoh, N. Hattori, M. Yanagiya and T. Matsumoto, Tetrahedron, 1985, 41, 3625) and by subsequent reaction with an amine HNR⁵R⁶.

Functional groups present in (I) which are not stable or are reactive under the reaction conditions of one or more of the reaction steps may be protected with appropriate protecting groups (as described e.g. in "Protective Groups in Organic Synthesis" by T. W. Greene and P. G. M. Wutts, 3rd Ed., 1999, Wiley, New York) before the critical step, applying methods well known in the art. Such protecting groups may be removed at a later stage of the synthesis using standard methods described in the literature.

An alternative method for the cleavage of Ugi reaction products is the treatment of amides such as K with sodium nitrite in a mixture of acetic acid and acetic acid anhydride to give an intermediate diazotisation reaction product which, after rearrangement, may be cleaved by reaction with a mixture of alkaline hydroxides (e.g. LiOH, NaOH, KOH) and hydrogen peroxide, to the corresponding free carboxylic acids L (Scheme 4, step a; see for example E. H. White *J. Am. Chem. Soc.* 1955, 77, 6011-6014; D. A: Evans, P. H. Carter, C. J. Dinsmore, J. C. Barrow, J. L. Katz, D. W. Kung *Tetrahedron Lett.* 1997, 38, 4535-4538). The amide cleavage reaction is broad with respect to the nature of the amide that can be employed and is by no means limited to benzylamides only.

An alternative method for the cleavage of Ugi reaction products is the treatment of amides such as K with di-tert-butyl dicarbonate in the presence of a suitable base, e.g. 4-N,N-dimethylaminopyridine, in a suitable solvent, e.g. acetonitrile, to give an intermediate tert-butyl-protected amide which may be cleaved by reaction with a mixture of alkaline hydroxides (e.g. LiOH, NaOH, KOH) and hydrogen peroxide, to the corresponding free carboxylic acids L (Scheme 2, step a; see for example D. L. Flynn, R. E. Zelle and P. A. Grieco, *J. Org. Chem.* 1983, 48, 2424). The amide cleavage reaction is broad with respect to the nature of the amide that can be employed and is by no means limited to benzylamides only.

Scheme 4

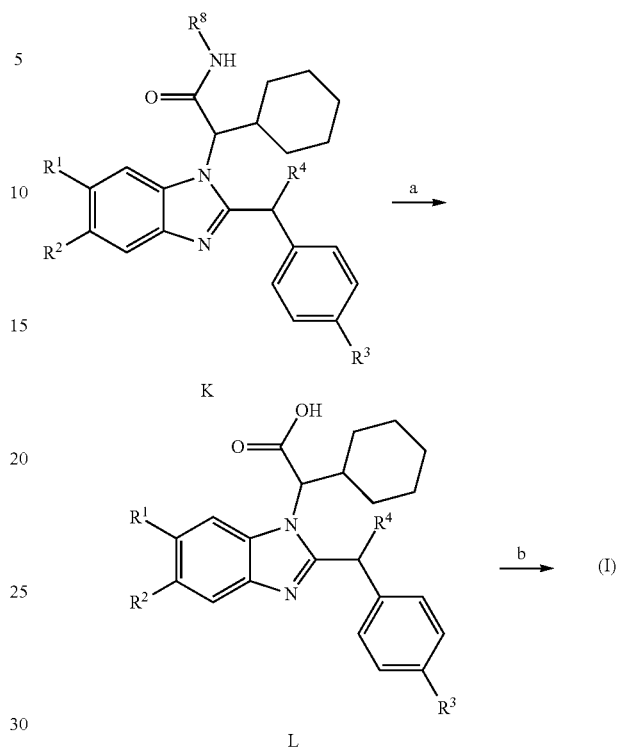

R⁸ = protecting group, such as e.g. optionally substituted benzyl

The application of chiral acids in the Ugi reaction step leads to the formation of diastereoisomers, which might be separable by standard chromatography on normal silica gel, either at the step of the amide K or the free acid L. Alternatively, chiral acids L may be resolved by standard methods known to the person skilled in the art, such as crystallisation with chiral amines, or by chiral chromatography.

The conversion of a compound of formula (I) into a pharmaceutically acceptable salt may be carried out by treatment with physiologically compatible bases. One possible method to form such a salt is for example by addition of 1/n equivalents of a basic salt such as e.g. M(OH)ₙ, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation; additionally, the pharmaceutically acceptable salt may be isolated by crystallisation from a suitable solvent or solvent mixture. Another possible method to form such a salt is for example by addition of an organic base such as lysine, arginine, diethanolamine, choline, guanidine and their derivatives etc.

The conversion of compounds of formula (I) into pharmaceutically acceptable esters can be carried out for example by treatment of carboxyl groups present in the molecules with an alcohol, such as methanol or ethanol, with a condensing reagent such as benzotriazol-1-yloxytris(dimethylamino) phosphonium hexafluorophosphate (BOP), N,N-dicylohexylcarbodiimide (DCC), N-(3-dimethylaminopropyl)-N'-ethyl-carbodiimide hydrochloride (EDCI) or O-(1,2-dihydro-2-oxo-1-pyridyl)-N,N,N,N-tetra-methyluronium-tetrafluorborate (TPTU) to produce the carboxylic ester. Alternatively, pharmaceutically acceptable esters of compounds of formula (I) may be obtained by the reaction of a mono tert-butyloxycarbonyl-protected ortho diamine A with a carboxylic acid B, an appropriately substituted isonitrile C, and an aldehyde D, as described above for the preparation of compounds of formula (I). Additionally, acceptable esters of compounds of formula (I) may be obtained by the reaction of a compound of formula L with an appropriately substituted amine as described above for the conversion of L into (I) (Scheme 4, step b).

Insofar as their preparation is not described in the examples, the compounds of formula (I) as well as all intermediate products can be prepared according to analogous methods or according to the methods set forth above. Starting materials are commercially available, are known in the art, or can be prepared by methods analogous to those described herein.

An alternative approach to the preparation of compounds of formula (I) is illustrated in Scheme 5.

A 2-azidoarylamine M, a carboxylic acid B, an isonitrile C and an aldehyde D are condensed in a suitable organic solvent, such as e.g. methanol, to provide N in a so-called Ugi-type reaction (Scheme 5, step a; typical procedures may e.g. be found in "The Peptides" by Gross & Meienhofer Vol. 2, Academic Press, N.Y., 1980, pp 365-381). In a subsequent intramolecular Staudinger-type reaction with a suitable reagent such as e.g. PPh$_3$, the azido bisamide N is converted to the benzimidazole (I) (Scheme 1, step b), which may optionally be N-alkylated by deprotonation with a strong base (e.g. NaH or LiHMDA) in a suitable solvent, and subsequent treatment with an alkylating agent $R^5$—X with X being a typical leaving group such as e.g. Cl, Br, I, —SO$_2$alkyl, —SO$_2$fluoroalkyl, —SO$_2$aryl (Scheme 5, step c).

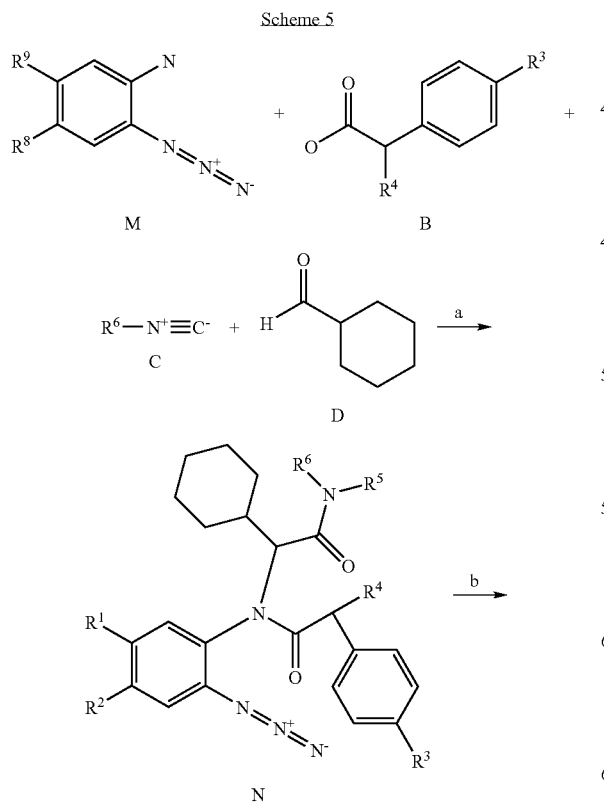

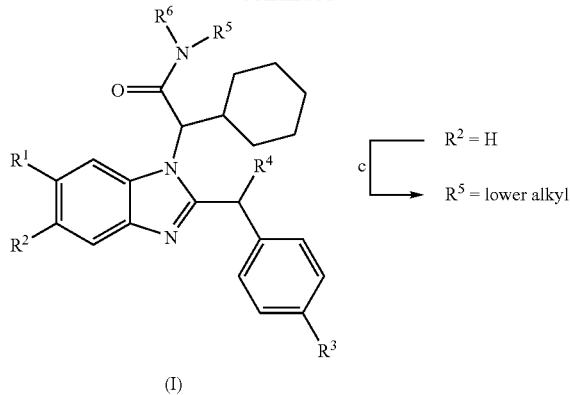

The 2-azidoarylamine M is usually prepared in three steps from the corresponding 2-aminoarylcarboxylic acid, which is converted into a 2-azidoarylcarboxylic acid by diazotisation with NaNO$_2$ in a suitable solvent (e.g. methanol) and subsequent treatment with a suitable azide salt such as NaN$_3$ or trimethylsilyl azide, or by reaction with tert-butyl nitrite and trimethylsilyl azide. The resulting 2-azidoarylcarboxylic acid is then converted into M via Curtius rearrangement of the 2-azidoarylcarboxylic azide obtained from the 2-azidoarylcarboxylic acid by its activation with a suitable reagent (e.g. chloroethylformate in the presence of a base such as triethylamine) and subsequent treatment with a suitable source of azide anions (e.g. NaN$_3$). The 2-azidoaryl amine M can alternatively be prepared via the 2-azidoarylcarboxamide obtained by activation of the 2-azidoarylcarboxylic acid with a suitable reagent (e.g. chloroethylformate in the presence of a base such as triethylamine) and subsequent treatment with ammonia. This amide is converted into M in a so called Hofmann-rearrangement by treatment with a suitable reagent such as NaOBr.

The invention also relates to a process for the manufacture of compounds of formula (I), which process comprises one of the following steps:

(a) The reaction of a compound of formula (II)

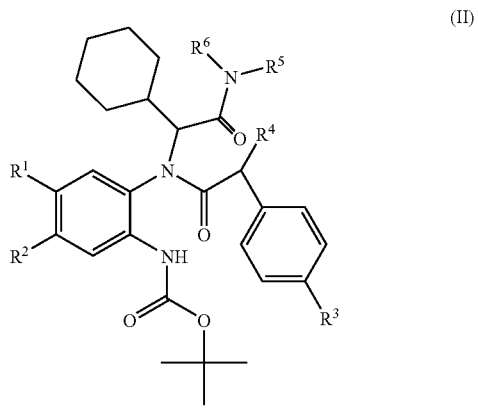

in the presence of an acid, optionally followed by the reaction of the resulting product with $R^5$—X in the presence of a base;

(b) The reaction of a compound of formula (III)

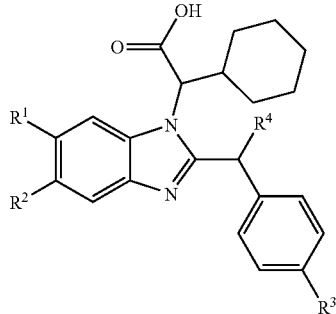

with $HNR^5R^6$ in the presence of a base and a peptide coupling agent;

(c) The reaction of a compound of formula (III)

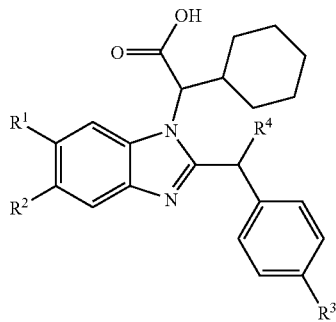

with thionyl chloride and pyridine to give a compound of formula (IV)

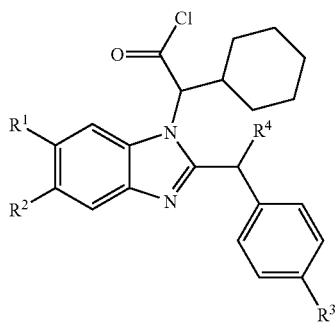

followed by the reaction of the compound of formula (IV) with $HNR^5R^6$ in the presence of a base;

(d) The reaction of a compound of formula (V)

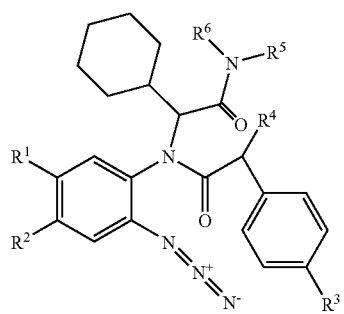

in the presence of a phosphine, optionally followed by the reaction of the resulting product with $R^5$—X in the presence of a base;

wherein $R^1$ to $R^6$ are as defined above and wherein X is a leaving group.

The acid in reaction (a) is preferably trifluoroacetic acid or hydrochloric acid. The base of reactions (a) and (d) is preferably NaH or lithium hexamethyldisilylamide (LiHMDA).

In step (b), the peptide coupling agent is preferably 1-(3-dimethylaminopropyl)-3-ethylcarbodiimide hydrochloride (EDCI) or N,N'-carbonyldiimidazole (CDI) and the base of is preferably an basic tertiary amine, preferably ethyldiisopropylamine.

The base of step (c) is preferably pyridine.

The phosphine of step (d) is preferably tributylphosphine or triphenylphosphine.

Preferably, the leaving group X is selected from Cl, Br, I, —$SO_2$alkyl, —$SO_2$fluoroalkyl and —$SO_2$aryl.

The invention also relates to compounds of formula (I), when manufactured by the process as defined above.

As described above, the novel compounds of the present invention have been found to bind to and selectively activate FXR. They can therefore be used in the treatment and prophylaxis of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

The compounds of the present invention are particularly active in the treatment and prophylaxis of dyslipidemia and diabetes type 2.

Also contemplated herein is combination therapy using one or more compounds or compositions provided herein, or a pharmaceutically acceptable derivative thereof, in combination with one or more of the following: cholesterol biosynthesis inhibitors (HMG CoA reductase inhibitors, e.g. lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g. thiazolidinediones e.g. rosiglitazone, troglitazone, and pioglitazone); PPAR alpha agonists (e.g. clofibrate, fenofibrate and gemfibronzil); PPAR dual alpha/gamma agonists (e.g. muraglitazar, aleglitazar, peliglitazar); bile acid sequestrants (e.g. anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-Coenzyme A:cholesterol O-acyl transferase (ACAT) inhibitors (e.g. avasimibe); selective estrogen receptor modulators (e.g. raloxifene or tamoxifen); LXR alpha or beta agonists, antagonists or partial agonists (e.g. 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g. metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g. pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g. sitagliptin phosphate, saxagliptin, vildagliptin, alogliptin or denagliptin), incretins (e.g. glucagon-like peptide-1 (GLP-1) receptor agonists (e.g. Exenatide (Byetta™), NN2211 (Liraglutide), GLP-1(7-36) amide and its analogs, GLP-1 (7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buproprion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, 5-HT$_{2C}$ (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g. orlistat); cyclooxygenase-2 (COX-2) inhibitors (e.g. rofecoxib and celecoxib); thrombin inhibitors (e.g. heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B12; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; agents other than LXR ligands that enhance ATP-Binding Cassette Transporter-Al gene expression; and bis-phosphonate compounds (e.g. alendronate sodium).

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

In another preferred embodiment, the invention relates to a method for the therapeutic and/or prophylactic treatment of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease, which method comprises administering an effective amount of a compound of formula (I).

The invention also embraces the use of compounds as defined above for the therapeutic and/or prophylactic treatment of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease.

The invention also relates to the use of compounds as described above for the preparation of medicaments for the therapeutic and/or prophylactic treatment of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease, Alzheimer's disease. Such medicaments comprise a compound as described above.

Prevention and/or treatment of high LDL cholesterol levels, high triglycerides, dyslipidemia, cholesterol gallstone disease, cancer, non-insulin dependent diabetes mellitus and metabolic syndrome is preferred, particularly high LDL cholesterol, high triglyceride levels and dyslipidemia.

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21(pLysS) cells by standard methods (Current Protocols in Molecular Biology, Wiley Press, ed. Ausubel et al.).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$, 0.01% CHAPS. For each reaction well in a 96-well plate, 40 nM of GST-FXR LBD fusion protein was bound to 10 µg glutathione ytrium silicate SPA beads (PharmaciaAmersham) in a final volume of 50 µl by shaking. A radioligand (e.g., 20 nM of 2,N-dicyclohexyl-2-[2-(2,4 dimethoxy-phenyl)-benzoimidazol-1-yl]-acetamide) and test compounds were added, and scintillation proximity counting was performed. All binding assays were performed in 96-well plates and the amount of bound ligand was measured on a Packard TopCount using OptiPlates (Packard). Dose response curves were performed within a range of test compound concentrations from $6\times10^{-9}$ M to $2.5\times10^{-5}$ M and $IC_{50}$ values were calculated.

The compounds according to formula (I) have an activity ($IC_{50}$) in the above assay, preferably of 0.1 nM to 25 µM, more preferably 0.1 nM to 10 µM, more preferably 0.1 nM to 100 nM.

For example, the following compounds showed the following $IC_{50}$ values in the assays described above:

| Example | FXR IC50 (µM) |
| --- | --- |
| 1A | 1.9 |
| 1B | 1.0 |
| 2A | 1.6 |
| 2B | 0.3 |
| 3A | 0.5 |
| 3B | 0.4 |
| 4A | 0.5 |
| 4B | 0.03 |
| 5A | 0.3 |
| 5B | 1.1 |
| 6A | 5 |
| 6B | 0.06 |
| 7A | 0.3 |
| 7B | 0.02 |
| 8A | 0.4 |
| 8B | 0.06 |
| 9A | 1.7 |

-continued

| Example | FXR IC50 (µM) |
| --- | --- |
| 9B | 2.6 |
| 10A | 0.2 |
| 10B | 0.1 |
| 11 | 21 |
| 12 | 6.8 |

The compounds of formula I and/or their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations

DMAP=4-dimethylaminopyridine, DMF=N,N-dimethylformamide, DMSO dimethyl sulfoxide, NaHCO$_3$=sodium hydrogen carbonate, Na$_2$SO$_4$=sodium sulfate, h=hour, HATU=1-[bis(dimethylamino)methylene]-1H-1,2,3-triazolo[4,5-b]pyridinium-3-oxide hexafluorophosphate, HCl=hydrogen chloride, HPLC=high performance liquid chromatography, ISP=ion spray positive (mode), ISN=ion spray negative (mode), min=minutes, LiOH=lithium hydroxide, MS=mass spectrum, NH$_4$Cl=ammonium chloride, NMR=nuclear magnetic resonance, P=protecting group, R=any group, rt=room temperature, SiO$_2$=silica gel, THF=tetrahydrofuran, X=halogen.

General Remarks

Reactions were carried out under nitrogen or argon atmosphere, when appropriate. If not mentioned otherwise, enantiomers or mixtures of distereoisomers were used for in vitro profiling.

Example 1

4-{(R)-2-Cyclohexyl-2-[5,6-difluoro-2-((S)-methoxy-phenyl-methyl)-benzoimidazol-1-yl]-acetylamino}-benzoic acid and 4-{(S)-2-Cyclohexyl-2-[5,6-difluoro-2-((S)-methoxy-phenyl-methyl)-benzoimidazol-1-yl]-acetylamino}-benzoic acid Step 1

(2-Amino-4,5-difluoro-phenyl)-carbamic acid tert-butyl ester

To a cooled (ice-bath) mixture of 1,2-diamino-4,5-difluorobenzene (10.00 g, 69 mmol, 1.0 equiv., [CAS RN 76179-40-3]) and di-tert-butyl-dicarbonate (12.87 g, 59 mmol, 0.85 equiv; [CAS RN 24424-99-5]) in absolute ethanol (150 ml) was added iodine (0.18 g, 0.007 mmol, 0.01 equiv. [CAS RN 7553-56-2]). The mixture was maintained overnight in the refrigerator. The solvent was evaporated under reduced pressure and the residue was purified by column chromatography on silica gel (500 g, 1:0 to 19:1 CH$_2$Cl$_2$/AcOEt eluant) to afford, in order of elution, the bis-boc derivative as an orange solid (1.58 g, 6%), and the desired compound as a white solid (12.58 g, 74%). $^1$H NMR (300 MHz, DMSO): δ 1.46 (s, 9H), 5.03 (br s, 2H), 6.65 (dd, J=8.2 Hz, J=12.9 Hz, 1H), 7.30 (dd, J=8.9 Hz, J=12.3 Hz, 1H), 8.38 (br s, 1H). MS (ISN): 243.4 [M–H]$^-$.

Step 2

N-Benzyl-2-cyclohexyl-2-[5,6-difluoro-2-((S)-methoxy-phenyl-methyl)-benzoimidazol-1-yl]-acetamide To a mixture of (2-amino-4,5-difluoro-phenyl)-carbamic acid tert-butyl ester (1.00 g, 4 mmol, 1.0 equiv) and (S)-alpha-methoxyphenylacetic acid (0.68 g, 1.0 equiv., [CAS RN 26164-26-1]) in methanol (25 mL) were added cyclohexanecarbaldehyde (0.459 g, 4 mmol, 1.0 equiv; [2043-61-0]) and benzyl isonitrile (0.48 g, 1.0 equiv., 4 mmol, CAS RN 10340-91-7). The mixture was stirred overnight at room temperature. A solution of 4 M HCl in dioxane (3 mL) was added, and the reaction mixture stirred at room temperature overnight. The mixture was partitioned between water (100 ml) and ethyl acetate (100 ml). The phases were separated and the aqueous phase extracted with ethyl acetate (2×50 ml), the combined organic phases washed with brine, dried over sodium sulfate and evaporated under reduced pressure to afford the title compound as an orange gum (2.16 g, quant., mixture of diastereomers) that was used without further purification. MS (ISP): 504.1 [M+H]$^+$.

Step 3

Cyclohexyl-[5,6-difluoro-2-((S)-methoxy-phenyl-methyl)-benzoimidazol-1-yl]-acetic acid To a solution of N-benzyl-2-cyclohexyl-2-[5,6-difluoro-2-((S)-methoxy-phenyl-methyl)-benzoimidazol-1-yl]-acetamide (2.16 g, 4 mmol, 1.0 equiv) in acetonitrile (25 ml) were added di-tert.-butyl-dicarbonate (1.123 g, 5 mmol, 1.2 equiv., [CAS RN 24424-99-5]) and N,N-dimethylaminopyridine ((0.051 g, 0.1 equiv., [CAS RN 1122-58-3]). The mixture was stirred 48 h at room temperature. A solution of lithium hydroxide monohydrate (0.54 g, 3.0 equiv., [CAS RN 1310-66-3]) in water (4 ml) was added, and the mixture vigorously stirred overnight at room temperature, and 2 h at 70° C. The mixture was allowed to cool to room temperature and poured into 1M aqueous hydrochloric acid (25 ml). The product was extracted with ethyl acetate (3×50 ml) and the combined organic phases washed with brine and dried over magnesium sulfate. The brown residue was purified by column chromatography on silica gel (75 g, 1:0 to 98:2 EtOAc/AcOH eluant) to afford the product as an off-white mixture of diastereomers. MS (ISN): 413.1 [M–H]$^-$.

Step 4

4-{2-Cyclohexyl-2-[5,6-difluoro-2-((S)-methoxy-phenyl-methyl)-benzoimidazol-1-yl]-acetylamino}-benzoic acid ethyl ester To a solution of cyclohexyl-[5,6-difluoro-2-((S)-methoxy-phenyl-methyl)-benzoimidazol-1-yl]-acetic acid (160 mg, 0.39 mmol, 1.0 equiv.) in dichloromethane (2 ml) was added pyridine (0.046 ml, 1.5 equiv.). Thionyl chloride (0.034 ml, 1.2 eq) was added dropwise. The mixture was stirred 1 h at room temperature. A solution of ethyl 4-amino-benzoate (64 mg, 0.95 equiv., [CAS RN 94-09-7]) and pyridine (0.031 ml, 1.1 equiv.) in dichloromethane (2 ml) was added and the mixture stirred overnight at room temperature. The mixture was applied to a 5 g silica gel column (Biotage) and the product eluted with EtOAc to afford the title compound as an orange solid that was used without further purification. MS (ISP): 562.3 [M+H]$^+$.

Step 5

4-{(R)-2-Cyclohexyl-2-[5,6-difluoro-2-((S)-methoxy-phenyl-methyl)-benzoimidazol-1-yl]-acetylamino}-benzoic acid and 4-{(S)-2-Cyclohexyl-2-[5,6-difluoro-2-((S)-methoxy-phenyl-methyl)-benzoimidazol-1-yl]-acetylamino}-benzoic acid To a solution of 4-{2-cyclohexyl-2-[5,6-difluoro-2-((S)-methoxy-phenyl-methyl)-benzoimidazol-1-yl]-acetylamino}-benzoic acid ethyl ester in water and tetrahydrofuran (1:1, 5 ml) was added aq. sodium hydroxide solution (2M, 2 eq). The mixture was shaken overnight at room temperature and 3 h at 55° C. The reaction was quenched by the addition of 1M aqueous citric acid, the solvent evaporated to dryness under reduced pressure and the residue purified by preparative HPLC to afford the title compound as individual enantiomers. Diastereomer A: MS (ISP): 533.9 [M+H]$^+$. Diastereomer B: MS (ISP): 533.9 [M+H]$^+$.

Example 2

4-{(R)-2-Cyclohexyl-2-[5,6-difluoro-2-((R)-methoxy-phenyl-methyl)-benzo imidazol-1-yl]-acetylamino}-benzoic acid and 4-{(S)-2-Cyclohexyl-2-[5, 6-difluoro-2-((R)-methoxy-phenyl-methyl)-benzoimidazol-1-yl]-acetylamino}-benzoic acid The title compound was prepared in analogy to Example 1, replacing (S)-alpha-methoxyphenylacetic acid with (R)-alpha-methoxyphenylacetic acid [CAS RN 3966-32-3]. Diastereomer A: MS (ISP): 533.9 [M+H]$^+$. Diastereomer B: MS (ISP): 533.9 [M+H]$^+$.

Example 3

4-{(R)-2-Cyclohexyl-2-[5,6-difluoro-2-((S)-methoxy-phenyl-methyl)-benzoimidazol-1-yl]-acetylamino}-3-fluoro-benzoic acid and 4-{(S)-2-Cyclohexyl-2-[5,6-difluoro-2-((S)-methoxy-phenyl-methyl)-benzoimidazol-1-yl]-acetylamino}-3-fluoro-benzoic acid The title compound was prepared in analogy to Example 1, replacing ethyl 4-amino-benzoate with ethyl 4-amino-3-fluoro-benzoate ([CAS RN 73792-12-8]). Diastereomer A: MS (ISP): 551.9 [M+H]$^+$. Diastereomer B: MS (ISP): 551.9 [M+H]$^+$.

Example 4

4-{(R)-2-Cyclohexyl-2-[5,6-difluoro-2-((R)-methoxy-phenyl-methyl)-benzoimidazol-1-yl]-acetylamino}-3-fluoro-benzoic acid and 4-{(S)-2-Cyclohexyl-2-[5,6-difluoro-2-((R)-methoxy-phenyl-methyl)-benzoimidazol-1-yl]-acetylamino}-3-fluoro-benzoic acid The title compound was prepared in analogy to Example 1, replacing (S)-alpha-methoxyphenylacetic acid with (R)-alpha-methoxyphenylacetic acid [CAS RN 3966-32-3] and replacing ethyl 4-amino-benzoate with ethyl 4-amino-3-fluoro-benzoate ([CAS RN 73792-12-8]). Diastereomer A: MS (ISP): 551.9 [M+H]$^+$. Diastereomer B: MS (ISP): 551.9 [M+H]$^+$.

Example 5

4-{(R)-2-Cyclohexyl-2-[5,6-difluoro-2-((S)-methoxy-phenyl-methyl)-benzoimidazol-1-yl]-acetylamino}-3-methyl-benzoic acid and 4-{(S)-2-Cyclohexyl-2-[5,6-difluoro-2-((S)-methoxy-phenyl-methyl)-benzoimidazol-1-yl]-acetylamino}-3-methyl-benzoic acid The title compound was prepared in analogy to Example 1, replacing ethyl 4-amino-benzoate with methyl 4-amino-3-methyl-benzoate ([CAS RN 18595-14-7]). Diastereomer A: MS (ISP): 547.5 [M+H]$^+$. Diastereomer B: MS (ISP): 547.5 [M+H]$^+$.

Example 6

4-{(R)-2-Cyclohexyl-2-[5,6-difluoro-2-((R)-methoxy-phenyl-methyl)-benzoimidazol-1-yl]-acetylamino}-3-methyl-benzoic acid and 4-{(S)-2-Cyclohexyl-2-[5,6-difluoro-2-((R)-methoxy-phenyl-methyl)-benzoimidazol-1-yl]-acetylamino}-3-methyl-benzoic acid The title compound was prepared in analogy to Example 1, replacing (S)-alpha-methoxyphenylacetic acid with (R)-alpha-methoxyphenylacetic acid [CAS RN 3966-32-3] and replacing ethyl 4-amino-benzoate with methyl 4-amino-3-methyl-benzoate ([CAS RN 18595-14-7]). Diastereomer A: MS (ISP): 547.5 [M+H]$^+$. Diastereomer B: MS (ISP): 547.5 [M+H]$^+$.

Example 7

3-Chloro-4-{(R)-2-cyclohexyl-2-[5,6-difluoro-2-((S)-methoxy-phenyl-methyl)-benzoimidazol-1-yl]-acetylamino}-benzoic acid and 3-Chloro-4-{(S)-2-cyclohexyl-2-[5,6-difluoro-2-((S)-methoxy-phenyl-methyl)-benzoimidazol-1-yl]-acetylamino}-benzoic acid The title compound was prepared in analogy to Example 1, replacing ethyl 4-amino-benzoate with methyl 4-amino-3-chloro-benzoate ([CAS RN 84228-44-4]). Diastereomer A: MS (ISN): 567.8 [M−H]$^-$. Diastereomer B: MS (ISN): 567.8 [M−H]$^-$.

Example 8

3-Chloro-4-{(R)-2-cyclohexyl-2-[5,6-difluoro-2-((R)-methoxy-phenyl-methyl)-benzoimidazol-1-yl]-acetylamino}-benzoic acid and 3-Chloro-4-{(S)-2-cyclohexyl-2-[5,6-difluoro-2-((R)-methoxy-phenyl-methyl)-benzoimidazol-1-yl]-acetylamino}-benzoic acid The title compound was prepared in analogy to Example 1, replacing (S)-alpha-methoxyphenylacetic acid with (R)-alpha-methoxyphenylacetic acid [CAS RN 3966-32-3] and replacing ethyl 4-amino-benzoate with methyl 4-amino-3-chloro-benzoate ([CAS RN 84228-44-4]). Diastereomer A: MS (ISP): 567.8 [M−H]$^-$. Diastereomer B: MS (ISP): 567.8 [M−H]$^-$.

Example 9

6-{(R)-2-Cyclohexyl-2-[5,6-difluoro-2-((S)-methoxy-phenyl-methyl)-benzoimidazol-1-yl]-acetylamino}-nicotinic acid and 6-{(S)-2-Cyclohexyl-2-[5,6-difluoro-2-((S)-methoxy-phenyl-methyl)-benzoimidazol-1-yl]-acetylamino}-nicotinic acid The title compound was prepared in analogy to Example 1, replacing ethyl 4-amino-benzoate with methyl 6-aminonicotinate ([CAS RN 36052-24-1]). Diastereomer A: MS (ISP): 534.9 [M+H]$^+$. Diastereomer B: MS (ISP): 534.9 [M+H]$^+$.

Example 10

6-{(R)-2-Cyclohexyl-2-[5,6-difluoro-2-((S)-methoxy-phenyl-methyl)-benzoimidazol-1-yl]-acetylamino}-nicotinic acid and 6-{(S)-2-Cyclohexyl-2-[5,6-difluoro-2-((S)-methoxy-phenyl-methyl)-benzoimidazol-1-yl]-acetylamino}-nicotinic acid The title compound was prepared in analogy to Example 1, replacing (S)-alpha-methoxyphenylacetic acid with (R)-alpha-methoxyphenylacetic acid [CAS RN 3966-32-3] and replacing ethyl 4-amino-benzoate with methyl 6-aminonicotinate ([CAS RN 36052-24-1]). Diastereomer A: MS (ISP): 534.9 [M+H]$^+$. Diastereomer B: MS (ISP): 534.9 [M+H]$^+$.

Example 11

(trans-4-{2-Cyclohexyl-2-[5-fluoro-2-((R)-methoxy-phenyl-methyl)-benzoimidazol-1-yl]-acetylamino}-cyclohexyl)-acetic acid

Step 1

N-Benzyl-2-cyclohexyl-2-[5-fluoro-2-((R)-methoxy-phenyl-methyl)-benzoimidazol-1-yl]-acetamide To a solution of (2-amino-5-fluoro-phenyl)-carbamic acid tert-butyl ester (4.0 g, 17.68 mmol, 1.0 equiv; prepared as described in M. J. Bamford, M. J. Alberti, N. Bailey, S. Davies, D. K. Dean, A. Gaiba, S. Garland, J. D. Harling, D. K. Jung, T. A. Panchal, C. A. Parr, J. G. Steadman, A. K. Talde, J. T. Townsend, D. M. Wilson, J. Witherington *Bioorg. Med. Chem. Lett.* 2005, 15, 3402-3406) in methanol (50 mL) was added cyclohexanecarbaldehyde (1.98 g, 2.13 mL, 17.68 mmol, 1.0 equiv; [2043-61-0]) and the mixture stirred at rt. After 30 min, (R)-methoxy-phenyl-acetic acid (2.94 g, 17.68 mmol, 1.0 equiv; [CAS RN 3966-32-3]) and isocyanomethylbenzene (2.07 g, 2.15 mL, 17.68 mmol, 1.0 equiv; [931-53-3]) were added and stirring continued at rt for 2 h. A solution of 4 M HCl in dioxane (18 mL) was added and the reaction mixture stirred at rt overnight. The solution was concentrated by evaporation under reduced pressure, the pH adjusted to 9 by addition of a solution of 1 M NaHCO$_3$ and the aqueous layer extracted with dichloromethane. The combined organic phases were dried over MgSO$_4$ and concentrated by evaporation under reduced pressure. The crude material was purified by silica column chromatography using a MPLC system (CombiFlash Companion, Isco Inc.) eluting with a gradient of heptane (+1% triethylamine)/ethyl acetate to give 5.9 g (69%) of the title compound. $^1$H NMR (300 MHz, CDCl$_3$): δ 1.25 (t, J=7.5 Hz, 3H), 1.41 (t, J=7.5 Hz, 3H), 3.43 (s, 3H), 4.01 (q, J=7.5 Hz, 2H), 4.26 (q, J=7.5 Hz, 2H), 5.05 (s, 1H), 6.43-6.48 (m, 2H). MS (ISP): 486.4 [M+H]$^+$.

Step 2

Cyclohexyl-[5-fluoro-2-((R)-methoxy-phenyl-methyl)-benzoimidazol-1-yl]-acetic acid To a solution of N-benzyl-2-cyclohexyl-2-[5-fluoro-2-((R)-methoxy-phenyl-methyl)-benzoimidazol-1-yl]-acetamide (5.91 g, 12.17 mmol, 1.0 equiv) in a mixture of acetic acid (40 mL) and acetic acid anhydride (80 mL) was added at 0° C. in several small portions sodium nitrite (18.47 g, 267.76 mmol, 22.0 equiv) within 1 h. The reaction mixture was stirred overnight allowing to warm up to rt. The solution was concentrated by evaporation under reduced pressure, the pH adjusted to 9 by addition of a solution of 1 M NaHCO$_3$ and the aqueous layer extracted with diethyl ether. The combined organic phases were dried over MgSO$_4$ and concentrated by evaporation under reduced pressure. The crude material was taken up in a mixture of THF:water (3:1, 40 mL) and a pre-prepared solution of LiOH (2.91 g, 121.71 mmol, 10.0 equiv) in hydrogen peroxide (2.76 g, 24.84 mL, 243.42 mmol, 20.0 equiv; 30% solution in water) was added and stirred at rt for 30 min. The solution was concentrated by evaporation under reduced pressure, the pH adjusted to 4 by addition of acetic acid and the aqueous layer extracted with diethyl ether. The combined organic phases were dried over MgSO$_4$ and concentrated by evaporation under reduced pressure. Purification by silica column chromatography using a MPLC system (CombiFlash Companion, Isco Inc.) eluting with a gradient of heptane (+1% acetic acid)/ethyl acetate yielded the title compound as two clean diastereoisomers in 1.52 g (32%, isomer A) and 1.50 g (31%, isomer B) together with a mixed fraction of 0.90 g (19%). Isomer A: MS (ISP): 397.3 [M+H]$^+$. Isomer B: MS (ISP): 397.1 [M+H]$^+$. Mixed fraction: MS (ISP): 397.1 [M+H]$^+$.

Step 3

(trans-4-{2-Cyclohexyl-2-[5-fluoro-2-((R)-methoxy-phenyl-methyl)-benzoimidazol-1-yl]-acetylamino}-cyclohexyl)-acetic acid ethyl ester To a solution of cyclohexyl-[5-fluoro-2-((R)-methoxy-phenyl-methyl)-benzoimidazol-1-yl]-acetic acid (350 mg, 0.88 mmol, 1.0 equiv) in DMF (5 mL) was added triethylamine (179 mg, 240 μL, 1.77 mmol, 2.0 equiv) and HATU (403 mg, 1.06 mmol, 1.2 equiv) and the mixture stirred at 40° C. After 15 min, trans-(4-amino-cyclohexyl)-acetic acid ethyl ester hydrochloride (235 mg, 1.06 mmol, 1.2 equiv; [CAS RN 76308-26-4]) was added and stirring continued at 50° C. for 2 h. The solution was concentrated by evaporation under reduced pressure, the pH adjusted to 9 by addition of a solution of 1 M NaHCO$_3$ and the aqueous layer extracted with dichloromethane. The combined organic phases were dried over MgSO$_4$ and concentrated by evaporation under reduced pressure. The crude material was used in the consecutive step without further purification. MS (ISP): 564.7 [M+H]$^+$.

Step 4

To a solution of (trans-4-{2-cyclohexyl-2-[5-fluoro-2-((R)-methoxy-phenyl-methyl)-benzoimidazol-1-yl]-acetylamino}-cyclohexyl)-acetic acid ethyl ester (190 mg, 0.34 mmol, 1.0 equiv) in acetonitrile (3 mL) was added a solution of 1 M LiOH (2 mL) and the reaction mixture heated by microwave irradiation to 110° C. for 30 min. A solution of 1 M HCl (25 mL) was added, the organic solvents removed by evaporation under reduced pressure and the residue extracted with ethyl acetate. The organic layer was washed with water, dried over Na$_2$SO$_4$ and concentrated by evaporation under reduced pressure yielding 138 mg (76%) of the title compound. MS (ISP): 536.4 [M+H]$^+$.

Example 12 trans-4-{2-Cyclohexyl-2-[5-fluoro-2-((R)-methoxy-phenyl-methyl)-benzoimidazol-1-yl]-acetylamino}-cyclohexanecarboxylic acid

Step 1 trans-4-{2-Cyclohexyl-2-[5-fluoro-2-((R)-methoxy-phenyl-methyl)-benzoimidazol-1-yl]-acetylamino}-cyclohexanecarboxylic acid ethyl ester The title compound was prepared in analogy to Example 11, Step 3, replacing trans-(4-amino-cyclohexyl)-acetic acid ethyl ester hydrochloride with trans-4-amino-cyclohexanecarboxylic acid ethyl ester ([CAS RN 2084-28-8]). MS (ISP): 550.7 [M+H]$^+$.

Step 2

The title compound was prepared in analogy to Example 11, Step 4. MS (ISP): 522.4 [M+H]$^+$

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I)

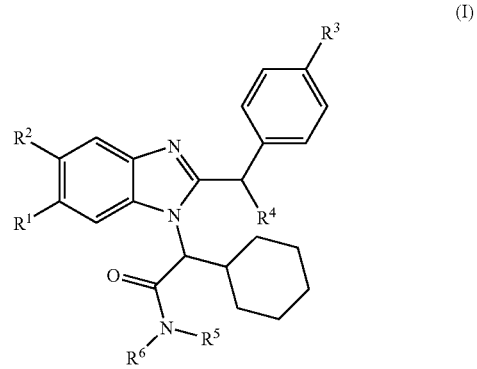

wherein
$R^1$ is hydrogen or halogen;
$R^2$ is hydrogen or halogen;
$R^3$ is hydrogen or halogen;
$R^4$ is hydroxy or alkoxy;
$R^5$ is hydrogen or alkyl;
$R^6$ is cyclohexyl, phenyl or pyridyl, wherein said cyclohexyl, phenyl and pyridyl are substituted with carboxy, carboxyalkyl, carboxyalkoxy, or carboxycycloalkoxy, and wherein said cyclohexyl, phenyl and pyridyl are optionally further substituted with one or two substituents independently selected from halogen, alkyl, haloalkyl, alkoxy, haloalkoxy and cyano;

or a pharmaceutically acceptable salt or ester thereof.

2. The compound according to claim 1, wherein $R^6$ is of formula (II)

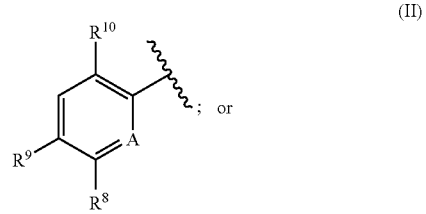

of formula (III)

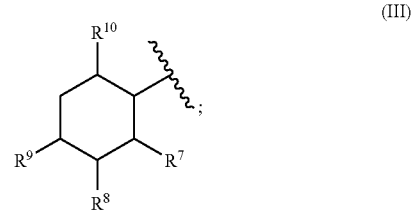

wherein
A is nitrogen or $CR^7$;
$R^7$ is hydrogen, halogen, alkyl, haloalkyl, alkoxy, haloalkoxy or cyano;
$R^{10}$ is hydrogen, halogen, alkyl, haloalkyl, alkoxy, haloalkoxy or cyano;

and wherein
one of $R^8$ and $R^9$ is selected from, carboxy, carboxyalkyl, carboxyalkoxy and carboxycycloalkoxy and the other one is hydrogen.

3. The compound according to claim 2 wherein $R^6$ is of formula (II)

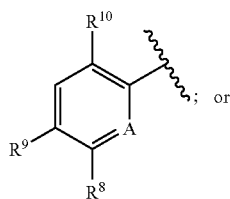

; or of formula (III)

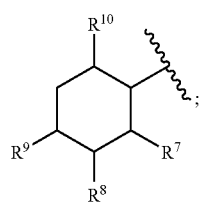

;

wherein
A is $CR^7$;
$R^7$ is hydrogen, halogen, alkyl, haloalkyl, haloalkoxy or cyano;
$R^{10}$ is hydrogen or halogen; and
one of $R^8$ and $R^9$ is selected from, carboxy, carboxyalkyl, carboxyalkoxy and carboxycycloalkoxy and the other one is hydrogen.

4. The compound according to claim 3 wherein
$R^7$ is hydrogen, fluorine, chlorine, methyl, trifluoromethyl, trifloromethoxy or cyano;
$R^{10}$ is hydrogen or fluorine; and
one of $R^8$ and $R^9$ is selected from, carboxy, carboxymethyl, carboxyethyl, carboxyethoxy and carboxycyclopropoxy and the other one is hydrogen.

5. The compound according to claim 1 wherein $R^4$ is hydroxy or methoxy.

6. The compound according to claim 1 wherein $R^3$ is hydrogen or fluorine.

7. The compound according to claim 1 wherein $R^1$ is fluorine.

8. The compound according to claim 1 wherein $R^2$ is fluorine.

9. The compound according to claim 1 wherein $R^5$ is hydrogen.

10. The compound according to claim 1 wherein $R^6$ is cyclohexyl, phenyl or pyridyl, wherein cyclohexyl, phenyl and pyridyl are substituted with, carboxy, carboxymethyl, carboxyethyl, carboxyethoxy, or carboxycyclopropoxy, and wherein and pyridyl are optionally further substituted with one or two substituents independently selected from fluoro, chloro, methyl, trifluoromethoxy, cyano and trifluoromethyl.

11. The compound according to claim 10, wherein $R^6$ is carboxycyclohexyl, carboxymethylcyclohexyl, carboxyphenyl, phenyl substituted with carboxy and fluoro, phenyl substituted with carboxy and methyl, phenyl substituted with carboxy and chloro, carboxypyridyl, phenyl substituted with carboxy and trifluoromethoxy, phenyl substituted with carboxy and cyano and fluoro, carboxyethoxyphenyl, phenyl substituted with carboxy and cyano, phenyl substituted with carboxy and trifluoromethyl, carboxycyclopropoxyphenyl or phenyl substituted with carboxyethyl and fluoro.

12. The compound according to claim 1 selected from
4-{(R)-2-Cyclohexyl-2-[5,6-difluoro-2-((S)-methoxy-phenyl-methyl)-benzoimidazol-1-yl]-acetylamino}-benzoic acid;
4-{(S)-2-Cyclohexyl-2-[5,6-difluoro-2-((S)-methoxy-phenyl-methyl)-benzoimidazol-1-yl]acetylamino}-benzoic acid;
4-{(R)-2-Cyclohexyl-2-[5,6-difluoro-2-((R)-methoxy-phenyl-methyl)-benzoimidazol-1-yl]-acetylamino}-benzoic acid;
4-{(S)-2-Cyclohexyl-2-[5,6-difluoro-2-((R)-methoxy-phenyl-methyl)-b enzoimidazol-1-yl]acetylamino}-benzoic acid;
4-{(R)-2-Cyclohexyl-2-[(5,6-difluoro-2-((S)-methoxy-phenyl-methyl)-benzoimidazol-1-yl]-acetylamino}-3-fluoro-benzoic acid;
4-{(S)-2-Cyclohexyl-2-[5,6-difluoro-2-((S)-methoxy-phenyl-methyl)-benzoimidazol-1-yl]-acetylamino}-3-fluoro-benzoic acid;
4-{(R)-2-Cyclohexyl-2-[5,6-difluoro-2-((R)-methoxy-phenyl-methyl)-benzoimidazol-1-yl]-acetylamino}-3-fluoro-benzoic acid;
4-{(S)-2-Cyclohexyl-2-[5,6-difluoro-2-((R)-methoxy-phenyl-methyl)-benzoimidazol-1-yl]-acetylamino}-3-fluoro-benzoic acid;
4-{(R)-2-Cyclohexyl-2-[5,6-difluoro-2-((S)-methoxy-phenyl-methyl)-benzoimidazol-1-yl]-acetylamino}-3-methyl-benzoic acid;
4-{(S)-2-Cyclohexyl-2 fluoro-2-[((S)-methoxy-phenyl-methyl)-benzoimidazol-1-yl]-acetylamino}-3-methyl-benzoic acid;
4-{(R)-2-Cyclohexyl-2-[5,6-difluoro-2-((R)-methoxy-phenyl-methyl)-benzoimidazol-1-yl]-acetylamino}-3-methyl-benzoic acid;
4-{(S)-2-Cyclohexyl-2-[5,6-difluoro-2-((R)-methoxy-phenyl-methyl)-benzoimidazol-1-yl]-acetylamino}-3-methyl-benzoic acid;
3-Chloro-4-{(R)-2-cyclohexyl-2-[5,6-difluoro-2-((S)-methoxy-phenyl-methyl)-benzoimidazol-1-yl]-acetylamino}-benzoic acid;
3-Chloro-4-{(S)-2-cyclohexyl-2-[5,6-difluoro-2-((S)-methoxy-phenyl-methyl)-benzoimidazol-1-yl]-acetylamino}-benzoic acid;
3-Chloro-4-{(R)-2-cyclohexyl-2-[5,6-difluoro-2-((R)-methoxy-phenyl-methyl)-benzoimidazol-1-yl]-acetylamino}-benzoic acid;
3-Chloro-4-{(S)-2-cyclohexyl-2-[5,6-difluoro-2-((R)-methoxy-phenyl-methyl)-benzoimidazol-1-yl]-acetylamino}-benzoic acid;
6-{(R)-2-Cyclohexyl-2-[5,6-difluoro-2-((S)-methoxy-phenyl-methyl)-benzoimidazol-1-yl-]-acetylamino}-nicotinic acid;
6-{(S)-2-Cyclohexyl-2-[5,6-difluoro-2-((S)-methoxy-phenyl-methyl)-benzoimidazol-1-yl]-acetylamino}-nicotinic acid;
6-{(R)-2-Cyclohexyl-2-[5,6-difluoro-2-((S)-methoxy-phenylmethyl)-benzoimidazol-1-yl]-acetylamino}-nicotinic acid;
6-{(S)-2-Cyclohexyl-2-[5,6-difluoro-2-((S)-methoxy-phenyl-methyl)-benzoimidazol-1-yl]-acetylamino}-nicotinic acid;

(trans-4-{2-Cyclohexyl-2-[5-fluoro-2-((R)-methoxy-phenyl-methyl)-benzoimidazol-1-yl]-acetylamino}-cyclohexyl)-acetic acid;

trans-4-{2-Cyclohexyl-2-[5-fluoro-2-((R)-methoxy-phenyl-methyl)-benzoimidazol-1-yl]-acetylamino}-cyclohexanecarboxylic acid;

4-(2-Cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-hydroxy-methyl]-benzoimidazol-1-yl}-acetylamino)-3-fluoro-benzoic acid;

3-Chloro-4-(2-cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-hydroxy-methyl]-benzoimidazol-1-yl}-acetylamino)-3-methyl-benzoic acid;

3-(2-Cyclohexyl-2-{5,6-difluoro-2-[(4-fluoro-phenyl)-hydroxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-fluoro-benzoic acid;

3-Chloro-4-(2-cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-(5,6-difluoro-2-[(4-fluoro-phenyl)-methoxy-methyl]-benzoimidazol-1-yl)-acetylamino)-3-methyl-benzoic acid;

3-(2-Cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-trifluoromethoxy-benzoic acid;

3-Cyano-4-(2-cyclohexyl-2-{5,6-difluoro-2-[(4-fluoro-phenyl)-methoxy-methyl]-benzoimidazol-1-yl}-acetylamino)-5-fluoro-benzoic acid;

2-[4-(2-Cyclohexyl-2-{5,6-difluoro-2-[(4-fluoro-phenyl)-methoxy-methyl]-benzoimidazol-1-yl}-acetylamino)-phenoxy]-propionic acid;

6-(2-Cyclohexyl-2-{5,6-difluoro-2-[(4-fluoro-phenyl)-methoxy-methyl]-benzoimidazol-1-yl}-acetylamino)-nicotinic acid;

3-Cyano-4-(2-cyclohexyl-2-{5,6-difluoro-2-[(4-fluoro-phenyl)-methoxy-methyl]-benzoimidazol-1-yl}-acetylamino)-benzoic acid;

4-(2-Cyclohexyl-2-{5,6-difluoro-2-[(4-fluoro-phenyl)-methoxy-methyl]-benzoimidazol-1-yl}-acetylamino)-3-trifluoromethyl-benzoic acid;

1-[4-(2-Cyclohexyl-2-{5,6-difluoro-2-[(4-fluoro-phenyl)-methoxy-methyl]-benzoimidazol-1-yl}-acetylamino)-phenoxy]-cyclopropanecarboxylic acid;

3-[4-(2-Cyclohexyl-2-{5,6-difluoro-2-[(4-fluoro-phenyl)-methoxy-methyl]-benzoimidazol-1-yl}-acetylamino)-3-fluoro-phenyl]-propionic acid;

Trans-[4-(2-cyclohexyl-2-{5,6-difluoro-2-[(4-fluoro-phenyl)-hydroxy-methyl]-benzoimidazol-1-yl}-acetylamino)-cyclohexyl]-acetic acid; and

[4-(2-Cyclohexyl-2-{5,6-difluoro-2-[(4-fluoro-phenyl)-methoxy-methyl]-benzoimidazol-1-yl}-acetylamino)-cyclohexyl]-acetic acid.

13. The compound according to claim 12 selected from

4-{(S)-2-Cyclohexyl-2-[5,6-difluoro-2-((R)-methoxy-phenyl-methyl)-benzoimidazol-1-yl]-acetylamino}-benzoic acid;

4-{(S)-2-Cyclohexyl-2-[5,6-difluoro-2-((R)-methoxy-phenyl-methyl)-benzoimidazol-1-yl]-acetylamino}-3-fluoro-benzoic acid;

4-{(S)-2-Cyclohexyl-2-[5,6-difluoro-2-((R)-methoxy-phenyl-methyl)-benzoimidazol-1-yl]-acetylamino}-3-methyl-benzoic acid;

3-Chloro-4-{(S)-2-cyclohexyl-2-[5,6-difluoro-2-((R)-methoxy-phenyl-methyl)-benzoimidazol-1-yl]-acetylamino}-benzoic acid; and 6-{(S)-2-Cyclohexyl-2-[5,6-difluoro-2-((R)-methoxy-phenyl-methyl)-benzoimidazol-1-yl]-acetylamino}-nicotinic acid.

14. A process for the manufacture of compounds of formula (I) as defined in claim 1, which process comprises one of the following steps:

(a) the reaction of a compound of formula (II)

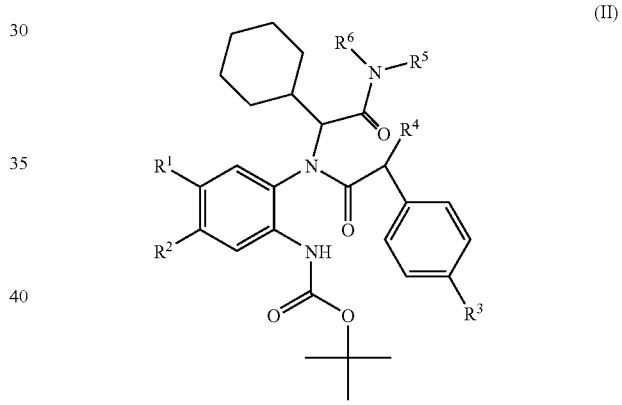

in the presence of an acid, optionally followed by the reaction of the resulting product with $R^5$—X in the presence of a base;

(b) the reaction of a compound of formula (III)

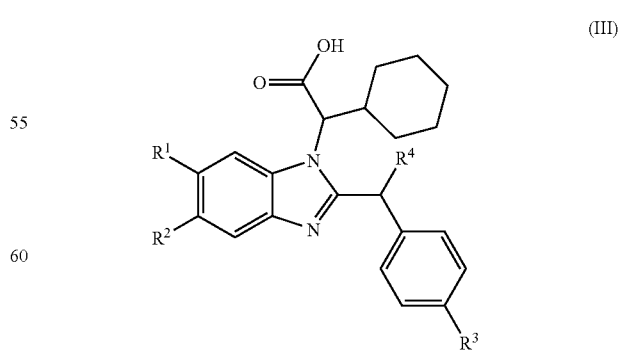

with $HNR^5R^6$ in the presence of a base and a peptide coupling agent;

(c) the reaction of a compound of formula (III)

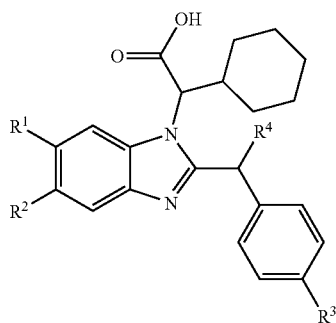

(III)

with thionyl chloride and pyridine to give a compound of formula (IV)

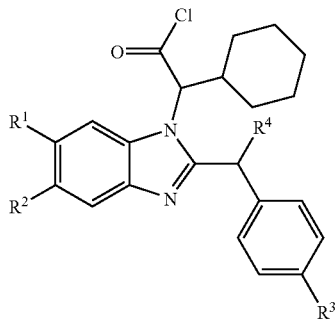

(IV)

followed by the reaction of the compound of formula (IV) with $HNR^5R^6$ in the presence of a base;

(d) the reaction of a compound of formula (V)

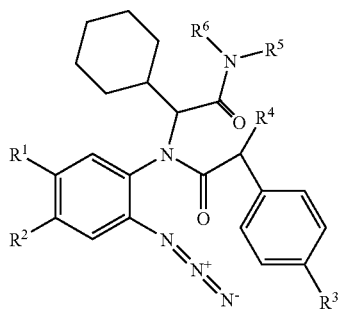

(V)

in the presence of a phosphine, optionally followed by the reaction of the resulting product with $R^5$—X in the presence of a base;

wherein $R^1$ to $R^6$ are as defined in claim 1 and wherein X is a leaving group.

15. A pharmaceutical composition comprising a compound according to claim 1 and a pharmaceutically acceptable carrier and/or adjuvant.

16. A method for the therapeutic treatment of diseases which are modulated by FXR agonists, said diseases selected from the group consisting of increased lipid and cholesterol levels, diabetes, particularly non-insulin dependent diabetes mellitus, diabetic nephropathy and obesity, which method comprises administering an effective amount of a compound as defined in claim 1 to a patient in need thereof.

* * * * *

UNITED STATES PATENT AND TRADEMARK OFFICE
CERTIFICATE OF CORRECTION

PATENT NO. : 8,143,422 B2  
APPLICATION NO. : 12/577765  
DATED : March 27, 2012  
INVENTOR(S) : Benson et al.

Page 1 of 1

It is certified that error appears in the above-identified patent and that said Letters Patent is hereby corrected as shown below:

In Claim 10, Col. 33, line 60, after the word, wherein insert -- phenyl --

In Claim 11, Col. 34, line 35, delete "4-{(S)-2-Cyclohexyl-2-fluro-2-[((S)-rnethoxy-phenyl-" and insert -- 4-{(S)-2-Cyclohexyl-5,6-difluoro-2-[((S)-methoxy-phenyl --

Signed and Sealed this
Eighth Day of May, 2012

David J. Kappos
*Director of the United States Patent and Trademark Office*